US009115202B2

(12) United States Patent
Segall et al.

(10) Patent No.: US 9,115,202 B2
(45) Date of Patent: *Aug. 25, 2015

(54) SOLUBLE CANOLA PROTEIN ISOLATE PRODUCTION FROM PROTEIN MICELLAR MASS

(75) Inventors: Kevin I. Segall, Winnipeg (CA); Brent E. Green, Winnipeg (CA); Martin Schweizer, Winnipeg (CA)

(73) Assignee: BURCON NUTRASCIENCE (MB) CORP., Winnipeg, Manitoba (CA)

( * ) Notice: Subject to any disclaimer, the term of this patent is extended or adjusted under 35 U.S.C. 154(b) by 4 days.

This patent is subject to a terminal disclaimer.

(21) Appl. No.: 12/737,533

(22) PCT Filed: Aug. 17, 2009

(86) PCT No.: PCT/CA2009/001152

§ 371 (c)(1),
(2), (4) Date: Mar. 24, 2011

(87) PCT Pub. No.: WO2010/020042

PCT Pub. Date: Feb. 25, 2010

(65) Prior Publication Data

US 2011/0172396 A1   Jul. 14, 2011

Related U.S. Application Data

(60) Provisional application No. 61/136,208, filed on Aug. 19, 2008.

(51) Int. Cl.
| | |
|---|---|
| *A23J 1/14* | (2006.01) |
| *C07K 14/415* | (2006.01) |
| *A23J 3/14* | (2006.01) |
| *A23L 2/66* | (2006.01) |

(52) U.S. Cl.
CPC .................. *C07K 14/415* (2013.01); *A23J 1/14* (2013.01); *A23J 3/14* (2013.01); *A23L 2/66* (2013.01)

(58) Field of Classification Search
USPC ........................................................ 426/656
See application file for complete search history.

(56) References Cited

U.S. PATENT DOCUMENTS

| | | | |
|---|---|---|---|
| 4,131,607 A | 12/1978 | Petit | |
| 4,208,323 A | 6/1980 | Murray | |
| 4,307,118 A | 12/1981 | Kajs | |
| 4,418,013 A * | 11/1983 | Cameron et al. | 530/377 |
| 4,889,921 A | 12/1989 | Diosady et al. | |
| 5,086,166 A | 2/1992 | Lawhon et al. | |
| 5,844,086 A | 12/1998 | Murray | |
| 6,005,076 A | 12/1999 | Murray | |
| 6,630,195 B1 | 10/2003 | Muralidhara | |
| 6,720,020 B2 | 4/2004 | Karleskind et al. | |
| 7,309,773 B2 | 12/2007 | Green et al. | |
| 2003/0015910 A1 | 1/2003 | Ichikawa | |
| 2003/0125526 A1 | 7/2003 | Barker et al. | |
| 2004/0034200 A1 | 2/2004 | Logie et al. | |
| 2004/0039174 A1 | 2/2004 | Barker et al. | |
| 2004/0077838 A1 | 4/2004 | Green et al. | |
| 2004/0254353 A1 | 12/2004 | Barker et al. | |
| 2005/0249828 A1 | 11/2005 | Logie et al. | |
| 2005/0255226 A1 * | 11/2005 | Schweizer et al. | 426/656 |
| 2009/0175999 A1 * | 7/2009 | Segall et al. | 426/590 |

FOREIGN PATENT DOCUMENTS

| | | |
|---|---|---|
| CA | 2467746 | 11/2002 |
| CA | 2488848 | 6/2003 |
| CA | 2553640 | 1/2005 |
| WO | WO 03/088760 | 10/2003 |

OTHER PUBLICATIONS

Asia Pacific Food Industry, Apr. 2001.

* cited by examiner

*Primary Examiner* — Tamra L Dicus
(74) *Attorney, Agent, or Firm* — William Kitt Sinden; Sim & McBurney

(57) ABSTRACT

A soluble canola protein isolate is prepared from canola protein micellar mass by solubilizing the protein micellar mass in a calcium salt solution, preferably a calcium chloride solution, followed by dilution of the resulting canola protein solution. Following removal of the precipitate phytic acid, the aqueous canola protein solution is concentrated, optionally diafiltered, and acidified to a pH of about 2.5 to 4.0 to produce an acidified clear canola protein solution, which may be concentrated, subjected to a color removal step and dried. The canola protein isolate so formed is soluble, transparent and heat stable in an acid aqueous environment and also is soluble at natural pH, without precipitation of protein.

16 Claims, No Drawings

SOLUBLE CANOLA PROTEIN ISOLATE PRODUCTION FROM PROTEIN MICELLAR MASS

REFERENCE TO RELATION APPLICATIONS

This application is a U.S. National Phase filing under 35 USC 371 of PCT/CA2009/001152 filed Aug. 17, 2009 claiming priority under 35 USC 119(e) from U.S. Provisional Application No. 61/136,208 filed Aug. 19, 2008.

FIELD OF INVENTION

This invention relates to the production of soluble canola protein isolate.

BACKGROUND TO THE INVENTION

Canola oil seed protein isolates having protein contents of at least 100 wt % (N×6.25) can be formed from oil seed meal by a process as described in copending U.S. patent application Ser. No. 10/137,391 filed May 3, 2002 (U.S. Patent Application Publication No. 2003-0125526 A1 and WO 02/089597) and U.S. patent application Ser. No. 10/476,230 filed Jun. 9, 2004 (U.S. Patent Application Publication No. 2004-0254353 A1), assigned to the assignee hereof and the disclosures of which are incorporated herein by reference. The procedure involves a multiple step process comprising extracting canola oil seed meal using an aqueous salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous, gluten-like protein micellar mass (PMM), and recovering the protein micellar mass from supernatant having a protein content of at least about 100 wt % (N×6.25). As used herein, protein content is determined on a dry weight basis. The recovered PMM may be dried.

In one embodiment of the process, the supernatant from the PMM settling step is processed to recover canola protein isolate from the supernatant. This procedure may be effected by initially concentrating the supernatant using an ultrafiltration membrane and drying the concentrate. The resulting canola protein isolate has a protein content of at least about 90 wt %, preferably at least about 100 wt % (N×6.25).

The procedures described in U.S. patent application Ser. No. 10/137,391 are essentially batch procedures. In copending U.S. patent application Ser. No. 10/298,678 filed Nov. 19, 2002 (U.S. Patent Application Publication No. 2004-0039174 A1 and WO 03/043439) and U.S. patent application Ser. No. 10/496,071 filed Mar. 5, 2005 (U.S. Patent Application Publication No. 2003-0015910 A1), assigned to the assignee hereof and the disclosures of which are incorporated herein by reference, there is described a continuous process for making canola protein isolates. In accordance therewith, canola oil seed meal is continuously mixed with an aqueous salt solution, the mixture is conveyed through a pipe while extracting protein from the canola oil seed meal to form an aqueous protein solution, the aqueous protein solution is continuously conveyed through a selective membrane operation to increase the protein content of the aqueous protein solution to at least about 50 g/L, while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is recovered from the settling vessel and may be dried. The PMM has a protein content of at least about 90 wt % (N×6.25), preferably at least about 100 wt %. The overflowed supernatant may be processed to recover canola protein isolate therefrom, as described above.

Canola seed is known to contain about 10 to about 30 wt % proteins and several different protein components have been identified. These proteins include a 12S globulin, known as cruciferin, a 7S protein and a 2S storage protein, known as napin. As described in copending U.S. patent application Ser. No. 10/413,371 filed Apr. 15, 2003 (U.S. Patent Application Publication No. 2004-0034200 A1 and WO 03/088760) and U.S. patent application Ser. No. 10/510,766 filed Apr. 29, 2005 (U.S. Patent Application Publication No. 2005-0249828 A1), assigned to the assignee hereof and the disclosures of which are incorporated herein by reference, the procedures described above, involving dilution of concentrated aqueous protein solution to form PMM and processing of supernatant to recover additional protein, lead to the recovery of isolates of different protein profiles.

In this regard, the PMM-derived canola protein isolate has a protein component composition of about 60 to about 98 wt % of 7S protein, about 1 to about 15 wt % of 12S protein and 0 to about 25 wt % of 2S protein. The supernatant-derived canola protein isolate has a protein component composition of about 60 to about 95 wt % of 2S protein, about 5 to about 40 wt % of 7S protein and 0 to about 5 wt % of 12S protein. Thus, the PMM-derived canola protein isolate is predominantly 7S protein and the supernatant-derived canola protein isolate is predominantly 2S protein. As described in the aforementioned U.S. patent application Ser. No. 10/413,371, the 2S protein has a molecular mass of about 14,000 daltons, the 7S protein has a molecular mass of about 145,000 daltons and the 12S protein has a molecular mass of about 290,000 daltons.

The PMM-derived canola protein isolate is largely insoluble in water at natural pH and is more soluble in acid aqueous media, such as uncarbonated and carbonated beverages, including soft drinks and sport drinks, but produces solutions of poor clarity. As such, the PMM-derived canola protein isolate is considered generally unsuitable for protein fortification of such beverages.

Canola is also known as rapeseed or oil seed rape.

SUMMARY OF INVENTION

We have now found a method for converting PMM into a form which is soluble and transparent and heat stable in an acidic aqueous environment and also soluble in water at natural pH. The resulting canola protein isolate is also low in phytic acid. Heat stability in solution at low pH, permits thermal processing, such as hot fill applications. The canola protein isolate is useful in products for human consumption, such as for the protein fortification of, in particular, soft drinks and sports drinks, as well as other aqueous systems, without precipitation of protein. The canola protein isolate is also useful for non-human food applications such as pet foods and aquaculture.

In accordance with one aspect of the present invention, there is provided a method of forming a canola protein isolate, which comprises:

(a) solubilizing a canola protein micellar mass, which may be in a dry or wet form, using about 1.5 to about 15 wt %, preferably about 2 to about 3 wt %, calcium chloride ($CaCl_2$) on a per protein basis and sufficient reverse osmosis RO purified water for an overall protein concentration of about 5 to about 50 wt %, preferably about 15 to about 25 wt %, and (b) diluting the resolubilized $CaCl_2$ treated protein micellar mass with up to about 20 volumes or more, preferably about 1 to about 3 volumes of RO water, (c) optionally removing any precipitate present, (d) optionally acidifying the resulting solution to a pH of about 2.5 to about 4, preferably about 2.9 to about 3.2, to produce an acidified clear canola protein solution, and (e) optionally concentrating the protein solution to about 5 to about 200 g/L, preferably about 80 to about 150 g/L and optionally diafiltering with RO water or with saline of approximately equal pH and conductivity to that of the protein solution, (f) optionally subjecting the clear concentrated canola protein solution to a colour removal step, and (g) optionally drying the concentrated canola protein solution.

The canola protein isolate provided herein is soluble in an acidic aqueous environment and is a novel product. Accordingly, in another aspect of the invention, there is provided a canola protein isolate having a protein content of at least about 90 wt % (N×6.25) d.b. and which consists predominantly of the 7S canola protein and which is soluble and heat stable in an acidic aqueous environment. The acidic aqueous environment may be a beverage having a pH of about 2.5 to about 5. The canola protein isolate may have a protein content of at least about 100 wt % (N×6.25) d.b.

The canola protein isolate produced according to the process herein may be used in conventional applications of protein isolates, such as, protein fortification of processed foods and beverages, emulsification of oils, body formers in baked goods and foaming agents in products which entrap gases. In addition, the canola protein isolate may be formed into protein fibers, useful in meat analogs, may be used as an egg white substitute or extender in food products where egg white is used as a binder. The canola protein isolate may be used as nutritional supplements. Other uses of the canola protein isolate are in pets foods, animal feed and in industrial and cosmetic applications and in personal care products.

The canola protein micellar mass may be prepared by the procedures described in above-mentioned U.S. patent application Ser. Nos. 10/137,371, 10/476,230, 10/298,678 and 10/496,071.

GENERAL DESCRIPTION OF INVENTION

The initial step of the process of providing the canola protein micellar mass involves solubilizing proteinaceous material from canola oil seed meal. The proteinaceous material recovered from canola seed meal may be the protein naturally occurring in canola seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as, potassium chloride, may be used. The salt solution has an ionic strength of at least about 0.05, preferably at least about 0.10, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen.

In view of the greater degree of dilution required for protein precipitation with increasing ionic strengths, it is usually preferred to utilize an ionic strength value less than about 0.8, and more preferably a value of about 0.1 to about 0.15.

In a batch process, the salt solubilization of the protein is effected at a temperature of from about 5° C. to about 75° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 75° C. is chosen due to the denaturation temperature of some of the present proteins.

In a continuous process, the extraction of the protein from the canola oil seed meal is carried out in any manner consistent with effecting a continuous extraction of protein from the canola oil seed meal. In one embodiment, the canola oil seed meal is continuously mixed with a food grade salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure is effected at temperatures between about 10° C. and about 75° C., preferably between about 15° C. and about 35° C.

The aqueous food grade salt solution generally has a pH of about 5 to about 6.8, preferably about 5.3 to about 6.2. The pH of the salt solution may be adjusted to any desired value within the range of about 5 to about 6.8 for use in the extraction step by the use of any convenient acid, usually hydrochloric acid, or alkali, usually sodium hydroxide, as required.

The concentration of oil seed meal in the food grade salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of phenolics in the protein solution.

The aqueous phase resulting from the extraction step then may be separated from the residual canola meal, in any convenient manner, such as by employing a decanter centrifuge, followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in U.S. Pat. Nos. 5,844,086 and 6,005,076, assigned to the assignee hereof and the disclosures of which are incorporated herein by reference, then the defatting steps described therein may be effected on the separated aqueous protein solution and on the concentrated aqueous protein solution discussed below. When the colour improvement step is carried out, such step may be effected after the first defatting step.

As an alternative to extracting the oil seed meal with an aqueous salt solution, such extraction may be made using water alone, although the utilization of water alone tends to extract less protein from the oil seed meal than the aqueous salt solution. Where such alternative is employed, then the salt, in the concentrations discussed above, may be added to the protein solution after separation from the residual oil seed meal in order to maintain the protein in solution during the concentration step described below. When a first fat removal step is carried out, the salt generally is added after completion of such operations.

Another alternative procedure is to extract the oil seed meal with the food grade salt solution at a relatively high pH value above about 6.8, generally up to about 9.9. The pH of the food grade salt solution may be adjusted to the desired alkaline value by the use of any convenient food-grade alkali, such as aqueous sodium hydroxide solution. Alternatively, the oil seed meal may be extracted with the salt solution at a relatively low pH below about pH 5, generally down to about pH 3. Where such alternative is employed, the aqueous phase resulting from the oil seed meal extraction step then is separated from the residual canola meal, in any convenient manner, such as by employing decanter centrifugation, followed by disc centrifugation and/or filtration to remove residual meal. The separated residual meal may be dried for disposal.

The aqueous protein solution resulting from the high or low pH extraction step then is pH adjusted to the range of about 5 to about 6.8, preferably about 5.3 to about 6.2, as discussed above, prior to further processing as discussed below. Such pH adjustment may be effected using any convenient acid, such as hydrochloric acid, or alkali, such as sodium hydroxide, as appropriate.

The aqueous protein solution is concentrated to increase the protein concentration thereof while maintaining the ionic strength thereof substantially constant. Such concentration generally is effected to provide a concentrated protein solution having a protein concentration of at least about 50 g/L, preferably at least about 200 g/L, more preferably at least about 250 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3,000 to about 100,000 daltons, preferably about 5,000 to about 10,000 daltons, having regard to differing membrane materials and configurations, and, for continuous operation, dimensioned to permit the desired degree of concentration as the aqueous protein solution passes through the membranes.

As is well known, ultrafiltration and similar selective membrane techniques permit low molecular weight species to pass through the membrane while preventing higher molecular weight species from so doing. The low molecular weight species include not only the ionic species of the food grade salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through having regard to the different membrane materials and configurations.

The concentrated protein solution then may be subjected to a diafiltration step using an aqueous salt solution of the same molarity and pH as the extraction solution. Such diafiltration may be effected using from about 2 to about 20 volumes of diafiltration solution, preferably about 5 to about 10 volumes of diafiltration solution. In the diafiltration operation, further quantities of contaminants are removed from the aqueous protein solution by passage through the membrane with the permeate. The diafiltration operation may be effected until no significant further quantities of contaminants and visible colour are present in the permeate. Such diafiltration may be effected using the same membrane as for the concentration step. However, if desired, the diafiltration step may be effected using a separate membrane with a different molecular weight cut-off, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentration step and the diafiltration step may be effected at any convenient temperature, generally about 20° to about 60° C., preferably about 20 to about 30° C., and for the period of time to effect the desired degree of concentration. The temperature and other conditions used to some degree depend upon the membrane equipment used to effect the concentration and the desired protein concentration of the solution.

The concentrated and optionally diafiltered protein solution may be subject to a further defatting operation, if required, as described in U.S. Pat. Nos. 5,844,086 and 6,005,076.

The concentrated and optionally diafiltered protein solution may be subject to a colour removal operation as an alternative to the colour removal operation described above. Powdered activated carbon may be used herein as well as granulated activated carbon (GAC). Another material which may be used as a colour adsorbing agent is polyvinyl pyrrolidone.

The colour adsorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour adsorbing agent, an amount of about 0.5% to about 5% w/v, preferably about 2% to about 3% w/v, may be used. The colour adsorbing agent may be removed from the canola protein solution by any convenient means, such as by filtration.

The concentrated and optionally diafiltered protein solution resulting from the optional colour removal step may be subjected to pasteurization to reduce the microbial load. Such pasteurization may be effected under any desired pasteurization conditions. Generally, the concentrated and optionally diafiltered protein solution is heated to a temperature of about 55° to about 70° C., preferably about 60° to about 65° C., for about 10 to about 15 minutes, preferably about 10 minutes. The pasteurized concentrated protein solution then may be cooled for further processing as described below, preferably to a temperature of about 25° to about 40° C.

Depending on the temperature employed in the concentration step and optional diafiltration step and whether or not a pasteurization step is effected, the concentrated protein solution may be warmed to a temperature of at least about 20°, and up to about 60° C., preferably about 25° to about 40° C., to decrease the viscosity of the concentrated protein solution to facilitate performance of the subsequent dilution step and micelle formation. The concentrated protein solution should not be heated beyond a temperature above which micelle formation does not occur on dilution by chilled water.

The concentrated protein solution resulting from the concentration step, and optional diafiltration step, optional colour removal step, optional pasteurization step and optional defatting step, then is diluted to effect micelle formation by mixing the concentrated protein solution with chilled water having the volume required to achieve the degree of dilution desired. Depending on the proportion of canola protein desired to be obtained by the micelle route and the proportion from the supernatant, the degree of dilution of the concentrated protein solution may be varied. With lower dilution levels, in general, a greater proportion of the canola protein remains in the aqueous phase.

When it is desired to provide the greatest proportion of the protein by the micelle route, the concentrated protein solution is diluted by about 5 fold to about 25 fold, preferably by about 10 fold to about 20 fold.

The chilled water with which the concentrated protein solution is mixed has a temperature of less than about 15° C., generally about 1° to about 15° C., preferably less than about 10° C., since improved yields of protein isolate in the form of protein micellar mass are attained with these colder temperatures at the dilution factors used.

In a batch operation, the batch of concentrated protein solution is added to a static body of chilled water having the desired volume, as discussed above. The dilution of the concentrated protein solution and consequential decrease in ionic strength causes the formation of a cloud-like mass of highly associated protein molecules in the form of discrete protein droplets in micellar form. In the batch procedure, the protein micelles are allowed to settle in the body of chilled water to form an aggregated, coalesced, dense, amorphous sticky gluten-like protein micellar mass (PMM). The settling may be assisted, such as by centrifugation. Such induced settling decreases the liquid content of the protein micellar mass, thereby decreasing the moisture content generally from about 70% by weight to about 95% by weight to a value of generally about 50% by weight to about 80% by weight of the total micellar mass. Decreasing the moisture content of the micellar mass in this way also decreases the occluded salt content of the micellar mass, and hence the salt content of dried isolate.

Alternatively, the dilution operation may be carried out continuously by continuously passing the concentrated protein solution to one inlet of a T-shaped pipe, while the diluting water is fed to the other inlet of the T-shaped pipe, permitting mixing in the pipe. The diluting water is fed into the T-shaped pipe at a rate sufficient to achieve the desired degree of dilution of the concentrated protein solution.

The mixing of the concentrated protein solution and the diluting water in the pipe initiates the formation of protein micelles and the mixture is continuously fed from the outlet from the T-shaped pipe into a settling vessel, from which, when full, supernatant is permitted to overflow. The mixture preferably is fed into the body of liquid in the settling vessel in a manner which minimizes turbulence within the body of liquid.

In the continuous procedure, the protein micelles are allowed to settle in the settling vessel to form an aggregated, coalesced, dense, amorphous, sticky, gluten-like protein micellar mass (PMM) and the procedure is continued until a desired quantity of the PMM has accumulated in the bottom of the settling vessel, whereupon the accumulated PMM is removed from the settling vessel. In lieu of settling by sedimentation, the PMM may be separated continuously by centrifugation.

The combination of process parameters of concentrating of the protein solution to a preferred protein content of at least about 200 g/L and the use of a dilution factor of about 10 to about 20, result in higher yields, often significantly higher yields, in terms of recovery of protein in the form of protein micellar mass from the original meal extract, and much purer isolates in terms of protein content than achieved using any of the known prior art protein isolate forming procedures discussed in the aforementioned US patents.

By the utilization of a continuous process for the recovery of canola protein isolate as compared to the batch process, the initial protein extraction step can be significantly reduced in time for the same level of protein extraction and significantly higher temperatures can be employed in the extraction step. In addition, in a continuous operation, there is less chance of contamination than in a batch procedure, leading to higher product quality and the process can be carried out in more compact equipment.

The settled PMM is separated from the residual aqueous phase or supernatant, such as by decantation of the residual aqueous phase from the settled mass or by centrifugation. The PMM may be used in the wet form or may be dried, by any convenient technique, such as spray drying or freeze drying, to a dry form. The dry PMM has a high protein content, in excess of about 90 wt % protein, preferably at least about 100 wt % protein (calculated as N×6.25), and is substantially undenatured (as determined by differential scanning calorimetry). The dry PMM isolated from fatty oil seed meal also has a low residual fat content, when the procedures of U.S. Pat. Nos. 5,844,086 and 6,005,076 are employed as necessary, which may be below about 1 wt %.

As described in the aforementioned U.S. patent application Ser. No. 10/413,371, the PMM consists predominantly of a 7S canola protein having a protein component composition of about 60 to 98 wt % of 7S protein, about 1 to about 15 wt % of 12S protein and 0 to about 25 wt % of 2S protein.

According to the present invention, the PMM is processed, in wet or dry form, to provide a clear solution which is either acidic or of natural pH. The natural pH solution, when dried, produces a product that can be resolubilized in water at natural pH or can later be acidified when reconstituted for its intended application in order to provide a clear acidic solution.

The PMM is initially solubilized using about 1.5 to about 15 wt %, preferably about 2 to about 3 wt % of a calcium salt on a per protein basis and sufficient water for an overall protein concentration of about 5 to about 50 wt %, preferably about 15 to about 25 wt %. The calcium salt added to the aqueous canola protein solution may be in any desired form, such as dried powder/flake or a concentrated aqueous solution thereof. The calcium salt conveniently is calcium chloride, although other calcium salts may be used.

After addition of the calcium chloride, the aqueous canola protein solution is diluted by about 1 to about 20 fold, preferably about 1 to about 3 fold to reduce the viscosity of the sample. Deposited calcium phytate present in the sample is removed from the diluted aqueous canola protein solution, such as by centrifugation and/or filtration, to yield a clear diluted aqueous canola protein solution, which may be dried by any convenient procedure, such as spray drying, to provide a canola protein isolate.

The pH of the clear diluted aqueous canola protein solution then is optionally adjusted to a value of about 2.0 to about 4.0, preferably about 2.9 to about 3.2. The pH adjustment may be effected in any convenient manner, such as by the addition of hydrochloric acid. The clear diluted aqueous canola protein solution remains clear to result in an acidified clear canola protein solution, which may be dried by any convenient procedure, such as spray drying, to provide a canola protein isolate.

The acidified clear canola protein solution or optionally natural pH solution is optionally concentrated to a concentration of about 50 to about 200 g/L, preferably about 80 to about 150 g/L, by using a selective membrane technique, such as described above for the concentration step during PMM formation.

The concentrated clear canola protein solution then may be subjected to a diafiltration step using water, acidified water or saline at the same pH and same or lower conductivity than the protein solution. Such diafiltration may be effected using from about 2 to about 20 volumes of diafiltration solution, preferably about 5 to about 10 volumes of diafiltration solution. In the diafiltration operation, further quantities of contaminants are removed from the aqueous solution by passage through the membrane with the permeate. The diafiltration operation may be effected until no significant further quantities of contaminants and visible colour are present in the permeate. Such diafiltration may be effected using the same membrane as for the concentration step. However, if desired, the diafiltration may be effected using a separate membrane, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration solution during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The resulting clear concentrated canola protein solution may be subjected to an optional colour removal step, such as that effected on the concentrated canola protein solution in the PMM-forming operation, using granulated activated carbon.

The concentrated optionally decolourized canola protein solution may be dried by any convenient procedure, such as by spray drying. The dry canola protein isolate has a high protein content, in excess of about 90 wt % protein, preferably at least about 100 wt % (N×6.25) d.b.

The canola protein isolate produced herein contains both albumin and globulin fractions and is soluble in an acidic aqueous environment, making the isolate ideal for incorporation into beverages, both carbonated and uncarbonated, to provide protein fortification thereto. Such beverages have a wide range of acidic pH values, ranging from about 2.5 to about 5. The canola protein isolate provided herein may be added to such beverages in any convenient quantity to provide protein fortification to such beverages, for example, at least about 5 g of the canola protein isolate per 12 fluid ounce quantity. The added canola protein isolate fully dissolves in the beverage and does not impair the clarity of the beverage, even after thermal processing. The canola protein isolate may be blended with dried beverage prior to reconstitution of the beverage by dissolution in water.

EXAMPLES

Example 1

This Example describes the preparation of a canola protein micellar mass from canola oil seed meal.

'a' kg of canola meal was added to 'b' L of 'c' M NaCl solution at ambient temperature and agitated for 30 minutes to provide an aqueous protein solution. The residual canola meal was removed and the resulting protein solution was partially clarified by centrifugation to produce 'd' L of partially clarified protein solution having a protein content of 'e' % by weight. The partially clarified protein solution was then filtered to further clarify resulting in a solution of volume 'f' having a protein content of 'g' by weight.

A 'h' L aliquot of the protein extract solution was reduced to 'i' kg by concentration on a polyethersulfone (PES) membrane having a molecular weight cutoff of 'j' daltons. The resulting concentrated protein solution had a protein content of 'k' % by weight.

The concentrated solution at 'l'° C. was diluted 'm' fold into cold RO water having a temperature 'n'° C. A white cloud formed immediately and was allowed to settle. The upper diluting water was removed and the precipitated, viscous, sticky mass (PMM) was recovered by centrifugation in a yield of 'o' wt % of the filtered protein solution. The parameters 'a' to 'o' are set forth in the following Table I:

TABLE I

| t | BW-SD084-E28-08A | BW-SA082-G14-08 | BW-SD087-G21-08A |
|---|---|---|---|
| a | 60 | 20 | 20 |
| b | 600 | 200 | 200 |
| c | 0.15 | 0.15 | 0.15 |
| d | 511 | 160 | 174 |
| e | 1.78 | 1.56 | 1.46 |
| f | 540 | 180 | 181 |
| g | 1.51 | 1.34 | 1.31 |
| h | 540 | 180 | 181 |

TABLE I-continued

| | | | |
|---|---|---|---|
| i | 32.68 | 8.28 | 8.28 |
| j | 100,000 | 100,000 | 100,000 |
| k | 18.64 | 22.29 | 22.86 |
| l | 30 | 29.8 | 30 |
| m | 1:15 | 1:15 | 1:15 |
| n | 2.2 | 1.5 | 2.4 |
| o | 3.4 | 51.5 | 30.0 |

Example 2

This Example describes the processing of the product from Example 1 into a canola protein isolate soluble in aqueous acid media.

'a' kg of the PMM from batch 'b' having a protein content of approximately 'c' wt % was resolubilized in 'd' L of 'e' M saline to provide a solution with a protein content of 'f' %.

The conductivity of this solution was then raised to 'g' mS by the addition of $CaCl_2$ from a concentrated solution prepared by dissolving 77 wt % flake $CaCl_2$ in RO water.

This 'h' L of solution was then diluted 'i' in 'j' L of room temperature RO water. Upon diluting, no pellet formed but the solution was quite cloudy. The greenish coloured precipitate was removed by centrifugation and filtration to produce 'k' L of clear solution having a protein content of 'l' wt %.

The clarified protein solution was then adjusted to pH 'm' with HCl. A PES membrane with a molecular weight cutoff of 10,000 Daltons was used to concentrate the pH 3 adjusted filtrate to approximately 'n' wt % protein in a volume of 'o' L.

A 'p' L aliquot of retentate was run through a 300 ml GAC column to determine if the GAC provided any colour or taste improvements. The GAC treated material was then spray dried to provide a dry product with a protein content of 'q' % (N×6.25) d.b. The product was given the designation 'b' C307C.

The remaining 'r' L of retentate was spray dried to provide dry product with a protein content of 's' % (N×6.25) d.b. The product was given the designation 'b' C307. The parameters 'a' to 's' are set forth in the following Table II:

TABLE II

| | |
|---|---|
| b | BW-SD084-E28-08A |
| a | 3 |
| c | 41 |
| d | 3 |
| e | 0.15 |
| f | 17.77 |
| g | 22.5 |
| h | 6 |
| i | 1:10 |
| j | 60 |
| k | 70 |
| l | 1.45 |
| m | 3 |
| n | 7.5 |
| o | 11 |
| p | 1 |
| q | 105.12 |
| r | 10 |
| s | 105.58 |

Example 3

This Example describes an alternate method of processing the product from Example 1 into a canola protein isolate soluble in aqueous acid media.

'a' kg of PMM from batch 'b' was resolubilized with 'c' wt % (on a per protein basis) $CaCl_2$ and 'd' L RO water to make a 'e' kg protein solution having a 'f' wt % protein content. The resolubilized PMM was diluted with 'g' volume(s) of room temperature RO water. A greenish coloured precipitate was removed by centrifugation. The resulting 'h' kg of centrate having a protein content of 'i' wt % was then adjusted to a pH of 'j' with HCL. The acidified clarified protein solution was then passed through 'k' L of granular activated carbon having the same pH and conductivity as the protein solution at a rate of 'l' BV/hr.

The GAC treated solution having a protein content of 'm' and mass of 'n' kg was then spray dried to produce a dry product with a protein content of 'o'% (N×6.25) d.b. The product was designated 'b' C307C. The parameters 'a' to 'o' are set forth in the following Table III:

TABLE III

| | |
|---|---|
| a | 1.58 |
| b | BW-SA082-G14-08A |
| c | 2.5 |
| d | 2.21 |
| e | 3.1 |
| f | 21.05 |
| g | 1 |
| h | 5.8 |
| i | 10.02 |
| j | 2.90 |
| k | 1.5 |
| l | 5 |
| m | 6.36 |
| n | 8.4 |
| o | 102.76 |

Example 4

This Example describes a method of processing the product from Example 1 into a natural pH canola protein isolate that can be used as is or acidified prior to application to produce a clear solution.

'a' kg of PMM from batch 'b' was resolubilized with 'c' wt % (on a per protein basis) $CaCl_2$ and 'd' L RO water to make a 'e' kg protein solution having a 'f' wt % protein content. The resolubilized PMM was diluted with 'g' volume(s) of room temperature RO water. A greenish coloured precipitate formed and was removed by centrifugation. The resulting 'h' kg of centrate having a protein content of 'i' wt % was then passed through 'j' L of granular activated carbon having the same pH and conductivity as the protein solution at a rate of 'k' BV/hr.

The GAC treated solution having a protein content of 'l' and mass of 'm' kg was then spray dried to produce a dry product with a protein content of 'n' % (N×6.25) d.b. The product was designated 'b' C307C. The parameters 'a' to 'n' are set forth in the following Table IV:

TABLE IV

| | |
|---|---|
| a | 1.57 |
| b | BW-SD087-G21-08A |
| c | 2.5 |
| d | 1.96 |
| e | 3.53 |
| f | 18.14 |
| g | 1 |
| h | 6.7 |
| i | 8.63 |
| j | 1.7 |
| k | 5 |
| l | 7.88 |
| m | 6.2 |
| n | 102.80 |

SUMMARY OF DISCLOSURE

In summary of this disclosure, the present invention provides a novel method for forming a canola protein isolate which is soluble and transparent and heat stable in an acidic aqueous environment and soluble in a natural pH aqueous environment from a canola protein micellar mass. Modifications are possible within the scope of the invention.

What we claim is:

1. A method of forming a canola protein isolate, which comprises:
   (a) solubilizing a canola protein micellar mass using an aqueous calcium salt solution of a concentration of about 1.5 to about 15 wt % of the protein present to form a canola protein solution having a protein concentration of about 5 to about 50 wt,
   (b) diluting the canola protein solution by about 1 to about 20 fold,
   (c) removing deposited phytic acid to provide a clear diluted aqueous canola protein solution,
   (d) adjusting the pH of the clear diluted aqueous canola protein solution to a value of about 2.0 to about 4.0 to result in an acidified clear canola protein solution,
   (e) concentrating the acidified clear canola protein solution to a concentration of about 50 to about 200 g/L by using a selective membrane technique to provide a concentrated clear diluted acidified canola protein solution,
   (f) subjecting the concentrated clear acidified aqueous canola protein solution to diafiltration using about 2 to about 40 volumes of diafiltration solution to provide a concentrated and diafiltered clear diluted acidified canola protein solution,
   (g) optionally subjecting the concentrated and diafiltered clear diluted acidified canola protein solution to a colour removal step, and
   (h) drying the concentrated and diafiltered clear diluted acidified protein solution to produce a canola protein isolate having a protein content of at least about 90 wt % (N×6.25) d.b.

2. The process claimed in claim 1 wherein said calcium salt is calcium chloride and is used in a concentration of about 2 to about 3 wt % of the protein present.

3. The process claimed in claim 2 wherein said canola protein solution has a protein concentration of about 15 to about 25 wt %.

4. The process claimed in claim 1 wherein said canola protein solution is diluted about 1 to about 3 fold.

5. The process of claim 1 wherein said clear diluted aqueous canola protein solution is dried to produce a canola protein isolate having a protein content of at least about 90 wt % (N×6.25) d.b.

6. The process of claim 1 wherein said clear diluted aqueous canola protein solution is concentrated to a concentration of about 50 to about 200 g/L by using a selective membrane technique to provide a concentrated clear aqueous canola protein solution.

7. The process of claim 6 wherein said clear diluted aqueous canola protein solution is concentrated to a concentration of about 80 to 150 g/L.

8. The process of claim 6 wherein said concentrated clear aqueous canola protein solution is subject to diafiltration using about 2 to about 20 volumes of diafiltration solution to provide a concentrated and diafiltered clear aqueous canola protein solution.

9. The process of claim 8 wherein said concentrated clear aqueous canola protein solution is subjected to diafiltration with about 5 to about 10 volumes of diafiltration solution.

10. The process of claim 8 wherein an antioxidant is present in the diafiltration solution during at least part of the diafiltration step.

11. The process of claim 8 wherein the concentrated and diafiltered clear aqueous canola protein solution is subjected to a colour removal step.

12. The process of claim 11 wherein the product of the colour removal step is dried to produce a canola protein isolate having a protein content of at least about 90 wt % (N×6.25) d.b.

13. The process claimed in claim 1 wherein the pH of the clear diluted aqueous canola protein solution is adjusted to a value of about 2.9 to about 3.2.

14. The process of claim 1 wherein said acidified clear canola protein solution is concentrated to a concentration of about 80 to 150 g/L.

15. The process of claim 1 wherein said concentrated clear diluted acidified canola protein solution is subjected to diafiltration with about 5 to about 10 volumes of diafiltration solution.

16. The process of claim 1 wherein an antioxidant is present in the diafiltration solution during at least part of the diafiltration step.

* * * * *